United States Patent [19]

Nakamura

[11] Patent Number: 5,475,725
[45] Date of Patent: Dec. 12, 1995

[54] PULSE METER WITH PEDOMETER FUNCTION

[75] Inventor: Chiaki Nakamura, Tokyo, Japan

[73] Assignee: Seiko Instruments Inc., Japan

[21] Appl. No.: 191,017

[22] Filed: Feb. 2, 1994

[30] Foreign Application Priority Data

Feb. 22, 1993 [JP] Japan .................................. 5-032310

[51] Int. Cl.$^6$ .............................. G01C 22/00; A61B 5/02
[52] U.S. Cl. .......................................... 377/24.2; 128/689
[58] Field of Search .......................... 377/24.2; 128/689, 128/668, 696

[56] References Cited

U.S. PATENT DOCUMENTS

| | | | |
|---|---|---|---|
| 4,312,358 | 1/1982 | Barney | 128/670 |
| 4,367,752 | 1/1983 | Jimenez et al. | 128/689 |
| 4,566,461 | 1/1986 | Lubell et al. | 128/689 |
| 4,807,639 | 2/1989 | Shimizu et al. | 128/690 |
| 4,855,942 | 8/1989 | Bianco | 377/24.2 |
| 4,962,469 | 10/1990 | Ono et al. | 364/561 |
| 4,974,601 | 12/1990 | Tranjan et al. | 128/696 |
| 5,164,967 | 11/1992 | Endo et al. | 377/24.2 |

OTHER PUBLICATIONS

Patent Abstracts of Japan, vol. 9, No. 253 (P–395) (1976) 11 Oct. 1985.
Patent Abstracts of Japan, vol. 5, No. 146 (P–80) (818) 16 Sep. 1981.

*Primary Examiner*—John S. Heyman
*Attorney, Agent, or Firm*—Adams & Wilks

[57] ABSTRACT

An electronic combined pulse meter and pedometer may be provided with only a single sensor used for determining walking pace and pulse rate. A pulse wave detector detects a pulse wave of the user and outputs a corresponding pulse wave signal to a calculating circuit and a walking state detector. The walking state detector compares the detected pulse wave with a reference level stored in a pulse wave level memory and outputs a walking state signal if the level of the detected pulse wave exceeds the reference level. Calculation control circuitry selects various constant values pre-stored in a constant value memory based upon the walking state signal and outputs the selected constant values to the calculating circuit and a display device. The calculating circuit calculates the time interval between successive pulses of the detected pulse wave signal in accordance with a clock signal and the selected constant values, and outputs the result to the display device.

19 Claims, 12 Drawing Sheets

F I G. 3
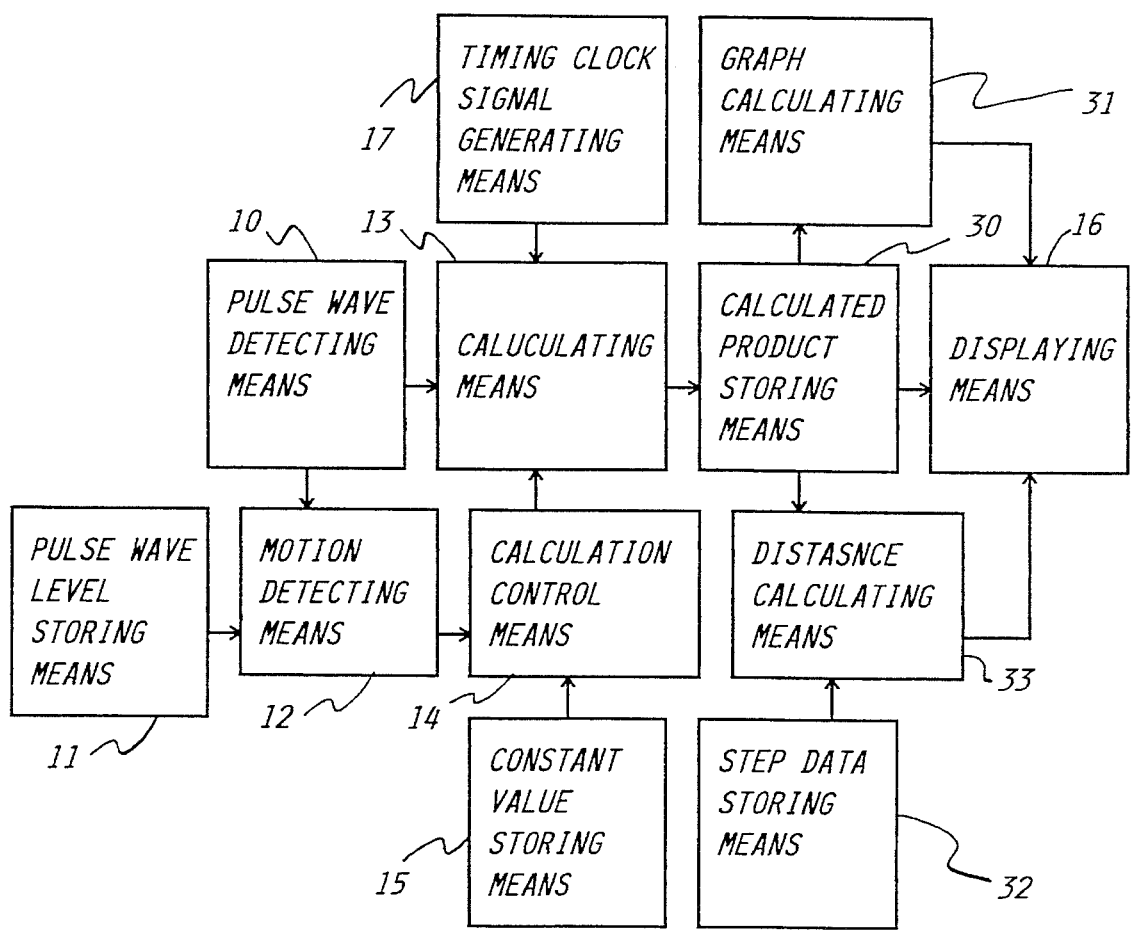

PULSE METER WITH PEDOMETER FUNCTION

BACKGROUND OF THE INVENTION

The present invention relates to a combined pulsimeter and pedometer which performs a walking pace calculation function as well as a pulse rate measurement function.

FIG. 4 is a functional block diagram illustrating the operation of a conventional pulsimeter with pedometer function. Pulse wave detecting means 40 detects an input pulse and outputs a corresponding pulse wave signal to an amplifying and wave shaping means 41. The amplifying and wave shaping means 41 outputs a wave-shaped pulse wave signal to a pulse rate calculating means 42. The pulse rate calculating means 42 calculates the time interval between successive pulse wave signals based on a timing clock signal provided by a timing clock signal generating means 45, and outputs calculated pulse rate data to a display selecting means 47. Walking pace detecting means 43 detects the impulses associated with steps and outputs a step signal to a wave shaping means 44. The wave shaping means 44 shapes the waveform of the step signal and outputs a wave-shaped step signal to a walking pace calculating means 46. The walking pace calculating means 46 calculates the time interval between successive step signals based on the timing clock signal provided by the timing pulse generating means 45, and outputs to the display selecting means 47 a calculated walking pace. The display selecting means 47 selects one of the pulse rate information and the walking pace information in response to an output level of a selecting switch 49, and outputs the selected information to a display means 48, which displays the selected information.

Such a pulsimeter with pedometer function is disclosed in unexamined Japanese Patent Laid Open No. JP-A-56-79382 (1981 official gazette). In the conventional pulsimeter with pedometer function described above, a pulse sensor for detecting the user's pulse wave and a separate and distinct impulse sensor for detecting the user's steps are needed. During operation, a pulse rate calculation function and a walking pace calculation function are manually selected alternatively by the manually operated selecting switch 49.

Recently, along with heightened individual health concerns, the popularity of exercise activity such as jogging has increased dramatically. In these exercise activities, pulse meters and pedometers are widely used since they provide indices for self health control.

The conventional pulsimeter with pedometer function, however, cannot be reduced in size due to the relatively large size of the impulse sensor and is more costly and time consuming to manufacture since the sensors for pulse wave detection and impulse detection are separate and distinct. In practical use, the conventional device is not easy to operate, since the selecting switch must be manually operated.

SUMMARY OF THE INVENTION

It is therefore an object of the present invention to provide a handy, portable pulsimeter with pedometer function which is simplified in construction and convenient in practical use.

In order to solve these problems, in one aspect of the present invention, a combined pulsimeter and pedometer is provided. The combined pulsimeter and pedometer comprises a pulse wave level storing means for storing a predetermined pulse wave amplitude level as a reference level for discriminating an output of a pulse wave detecting means as being indicative of an at rest condition of a user or as indicating that the user is walking, jogging or running. The pulse wave detecting means has a pulse wave sensor for detecting a pulse wave of a human body and producing a corresponding pulse wave signal. Motion detecting means is included for detecting motion of the human body by comparing the pulse wave signal output by the pulse wave detecting means with the reference level from the pulse wave level storing means and producing a motion signal when the level of the pulse wave signal exceeds the reference level. Calculating means is provided for calculating the time interval between consecutive pulses of the pulse wave signal, and a calculation control means is provided for controlling the calculating means in accordance with an output of the motion detecting means and for selecting a set of preset constant values for signal calculations in accordance with the output of the motion detecting means. The present invention is therefore able to perform a pulse rate measurement and a pace measurement with a single sensor included in the pulse wave detecting means.

In accordance with a second aspect of the present invention and in order to solve the problems noted above, the combined pulsimeter and pedometer further comprises motion timing means for measuring the time duration of the motion signal and the calculation control means controls the calculating means based on the output of the motion timing means and the output of the constant value storing means. In accordance with this aspect of the invention, the combined pulsimeter and pedometer automatically and stably switches between the alternate operations of a pedometer function and a pulsimeter function without responding to a momentary or abrupt change in the motion signal.

BRIEF DESCRIPTION OF THE DRAWINGS

FIG. 3 is a functional block diagram of a third embodiment of the present invention.

DETAILED DESCRIPTION OF THE PREFERRED EMBODIMENTS

Embodiments of this invention are explained hereinafter based on the drawings.

Figure 1:
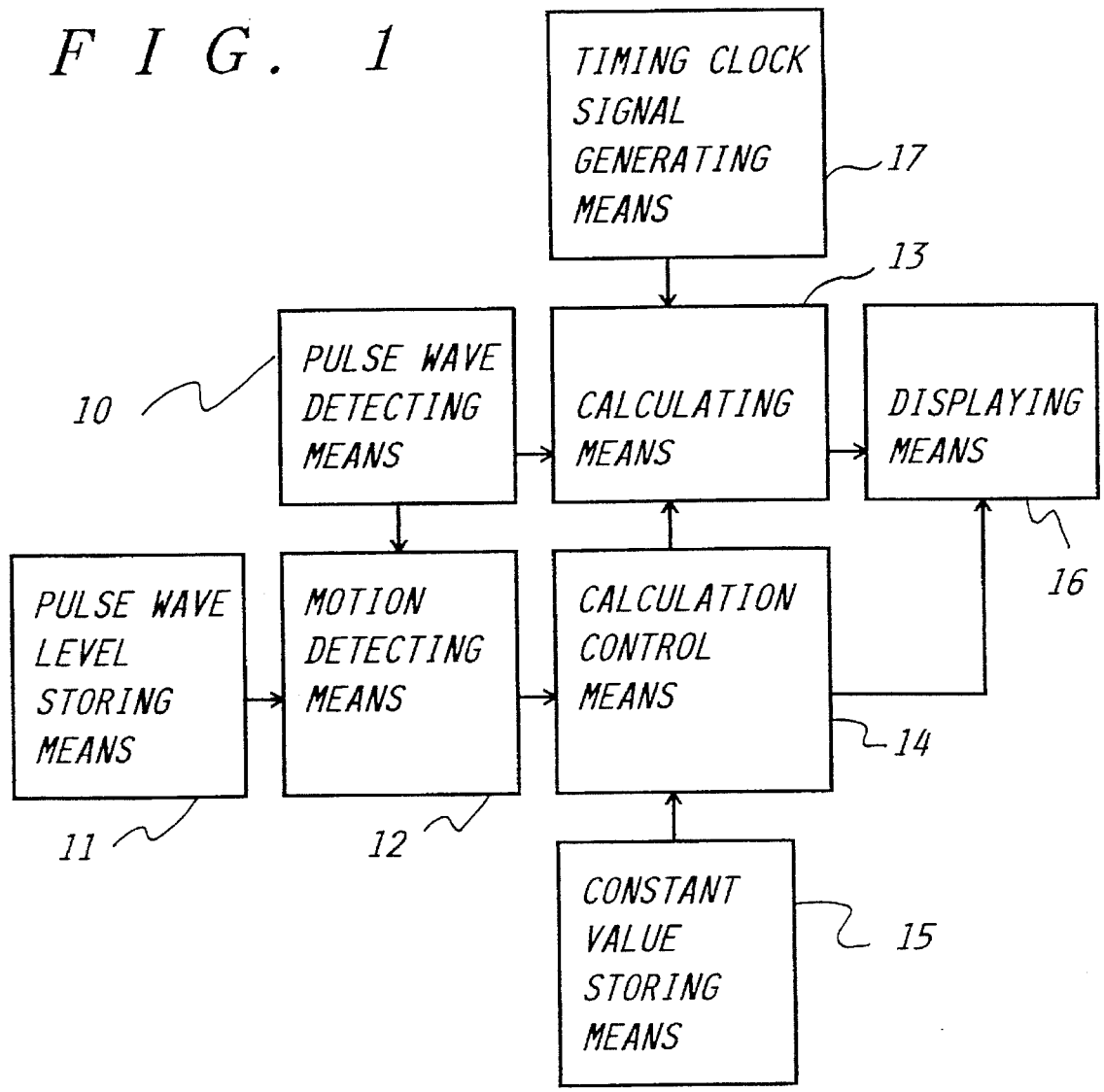
FIG. 1 is a functional block diagram of the combined pulsimeter and pedometer in accordance with a first embodiment of the present invention.

FIG. 1 is a functional block diagram which represents an example of a typical construction of the present invention. A pulse wave detecting means 10 detects a pulse wave of a human body and outputs a pulse wave signal to a motion detecting means 12 and a calculating means 13. The motion detecting means 12 outputs a motion signal to a calculation control means 14 by comparing the pulse wave signal with stored contents in a pulse wave level storing means 11. The calculation control means 14 selects, based on the motion signal input thereto, various constant values stored in a constant value storing means 15, and outputs the various constant values and the result of its selection to the calculating means 13 and the displaying means 16. The calculating means 13 calculates a time interval between consecutive pulse wave signals, based on a timing clock signal generated by a timing clock signal generating means 17 and the various constant values output by the calculation control means 14, and outputs calculated results to the displaying means 16.

The pulse wave detected by the pulse wave detecting means 10 reflects a pulse wave of a human body, i.e., a user, in case that the user is at rest. On the other hand, when the user is walking, the pulse wave reflects the motion, for example, of the swinging arms of the user.

Since a signal amplitude level of an output signal from the pulse wave detecting means is different in an at rest condition of the user from that of a walking condition of the user, the motion detecting means 12 determines which condition the detected pulse wave reflects by comparing the pulse wave signal with a reference level stored in a pulse wave level storing means 11. Accordingly, the displaying means 16 displays the user's pulse rate when the user is at rest, and displays the user's walking pace as well as an identifying walking mode marker when the motion detecting means detects a walking condition of the user based on the results of the comparison performed by the motion detecting means 12 by way of the calculation control means 14. The motion detecting means 12 can likewise detect not only a walking condition but also a jogging or running condition according to the stored reference level in the pulse wave level storing means 11.

Figure 2:
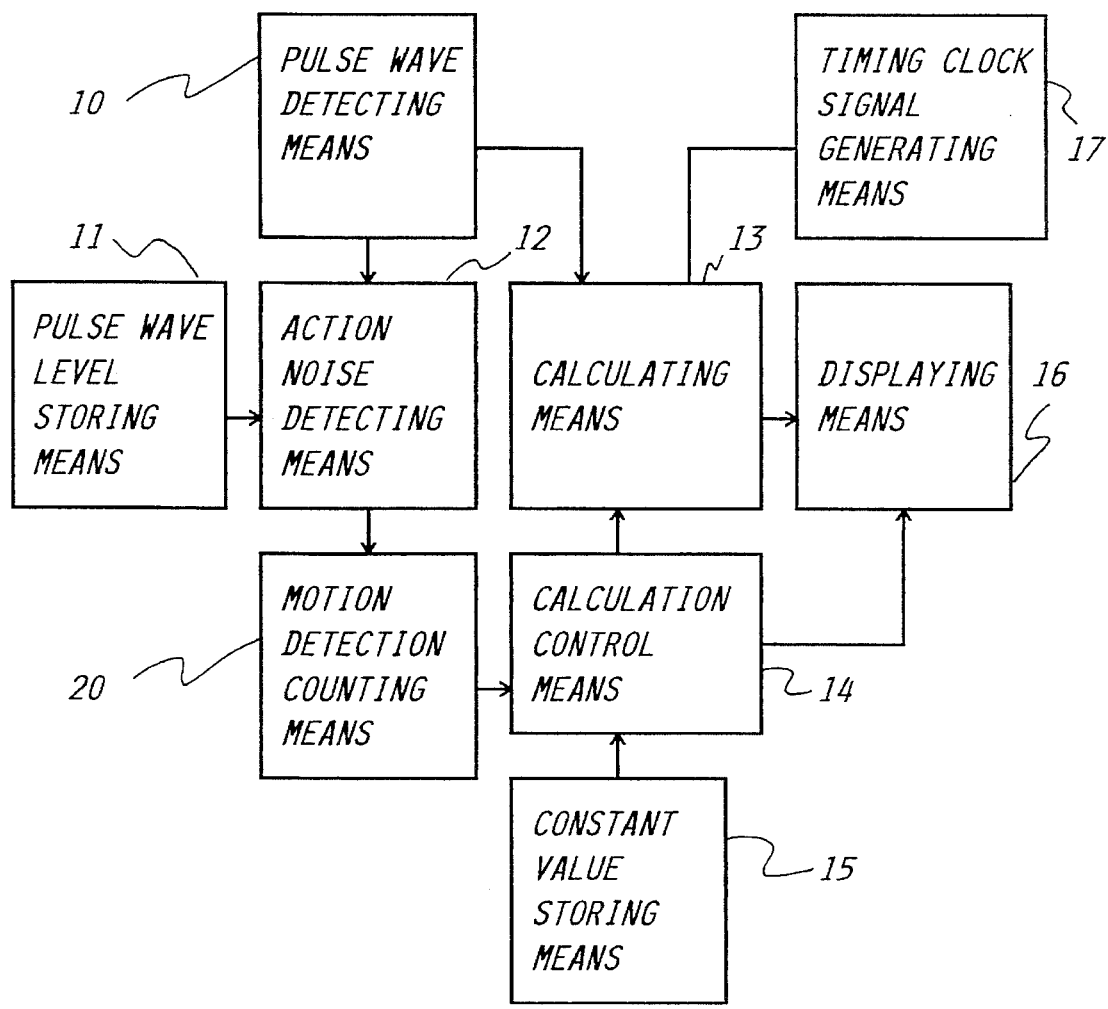
FIG. 2 is a functional block diagram of a second embodiment of the present invention.
Figure 4:
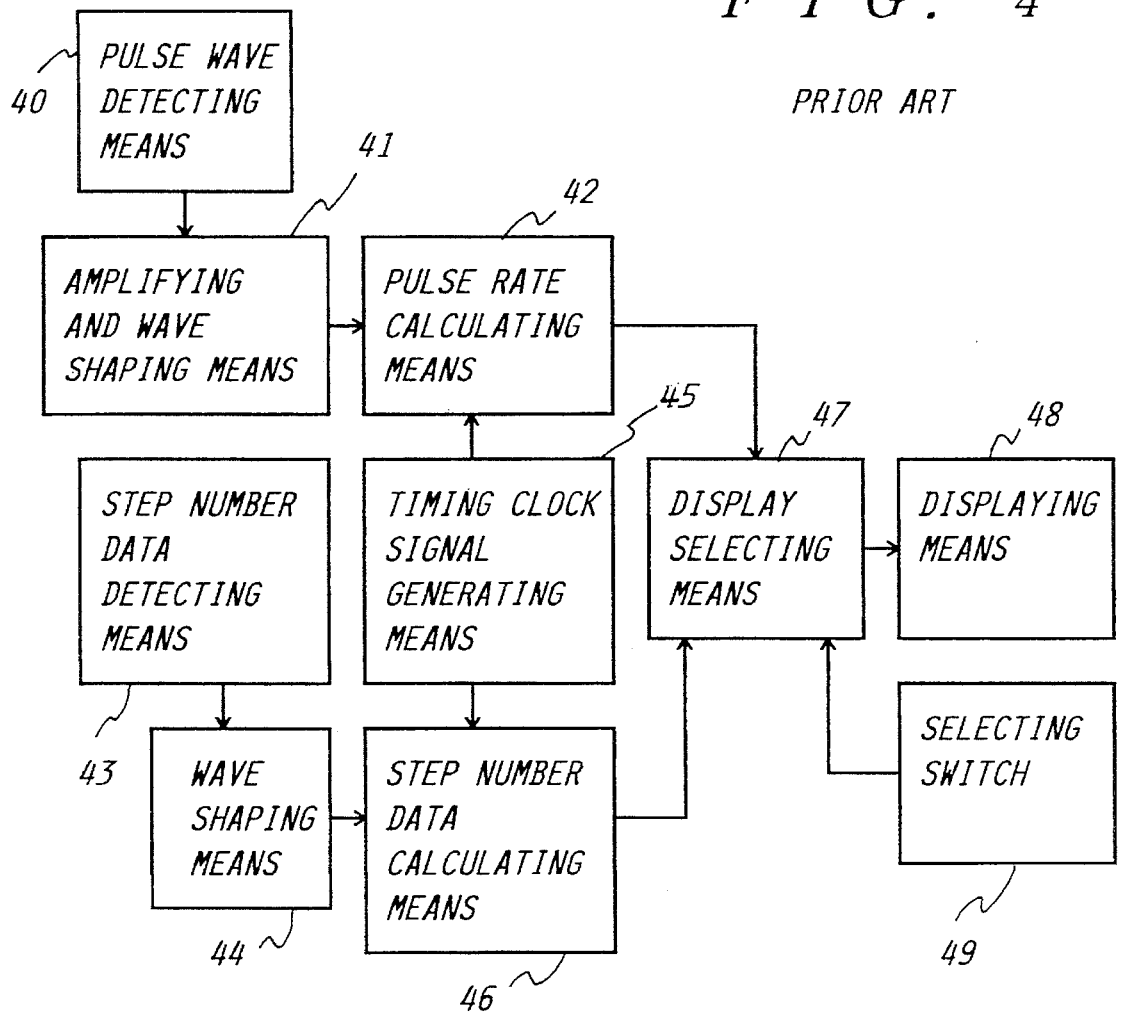
FIG. 4 is a functional block diagram of a conventional pulsimeter with pedometer function.

FIG. 2 is a functional block diagram of a second embodiment which represents another example of the typical construction of the present invention. The pulse wave detecting means 10 detects a pulse wave of a human body and outputs a corresponding pulse wave signal to the motion detecting means 12 and the calculating means 13. The motion detecting means 12 outputs a motion signal to a motion counting means 20 by comparing the pulse wave signal with stored contents in the pulse wave level storing means 11. The motion counting means 20 measures the time duration of the motion signal, i.e., the length of time that consecutive outputs of the pulse wave detecting means are discriminated as being indicative of motion based upon comparison with a predetermined level, and outputs a motion signal to the calculation control means 14 when the time duration exceeds a predetermined time. The calculation control means 14 selects, based on the motion signal, various constant values stored in the constant value storing means 15, and outputs the various constant values and the selected resultant to the calculating means 13 and the displaying means 16. The calculating means 13 calculates the time interval between consecutive pulse wave signals, based on a timing clock signal generated by the timing clock signal generating means 17 and the various constant values output by the calculation control means 14, and outputs calculated results to the displaying means 16.

Since the motion signal detected by the motion counting means 20 is maintained at a stable level without being affected by momentary or instantaneous change in the motion signal, displayed contents on the displaying means 16 do not vary momentarily or instantaneously.

FIG. 3 is a functional block diagram of a third embodiment, showing an example of a typical construction of the present invention. The pulse wave detecting means 10 detects a pulse wave of a human body and outputs a pulse wave signal to the calculating means 13 and the motion detecting means 12. The motion detecting means 12 compares the pulse wave signal with the stored contents in the pulse wave level storing means 11, and outputs a motion signal to the calculation control means 14. The calculation control means 14 selects, based on the motion signal, various constant values stored in the constant value storing means 15, and outputs the various constant values to the calculating means 13. The calculating means 13 calculates the time interval between consecutive pulse wave signals based both on the timing clock signal generated by the timing clock signal generating means 17 and the various constant values output by the calculation control means 14, and outputs the result to a calculated product storing means 30.

The calculated product storing means 30 stores the resultant product and, if necessary, outputs the stored contents to the displaying means 16, a graph calculating means 31 and a distance calculating means 33. The graph calculating means 31 calculates furthermore with the calculated and stored contents for the purpose of displaying time-series graph, and outputs the calculated result to the displaying means 16. The distance calculating means 33 calculates the distance that the user has walked, jogged or ran in accordance with the calculated and stored contents of the calculated product storing means 30 and the stored contents in a step span data storing means 32, and outputs the calculated result to the displaying means 16.

By means of the graph calculating means 31, and the distance calculating means 33, the pulsimeter with pedometer function of the present invention displays not only a pulse rate and a walking pace, but also time series changes in the above data as well as a walking distance. Therefore, the pulsimeter can be used as a distance finder.

(1) The first practical embodiment.

Figure 5:
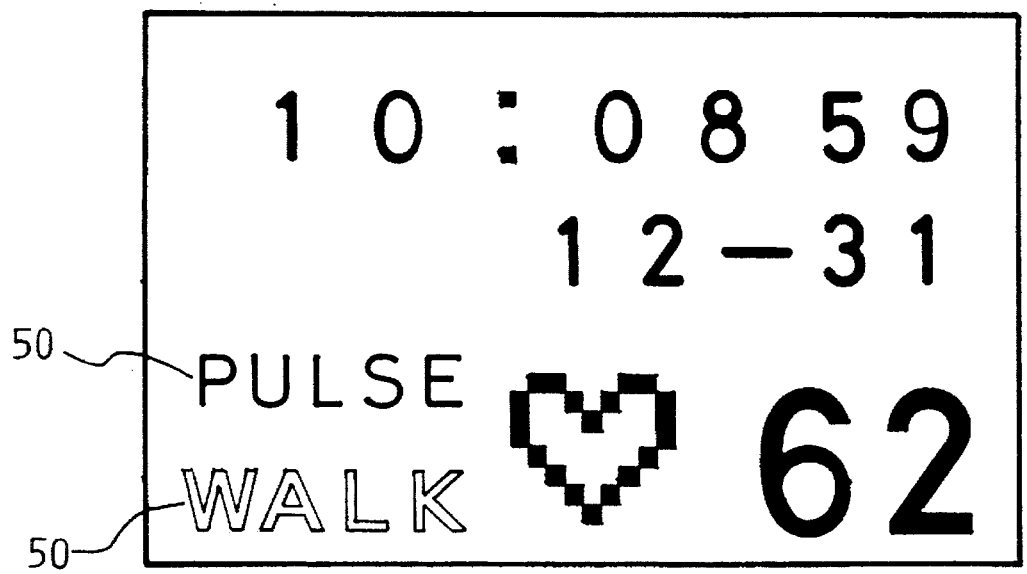
FIG. 5 is a display example of an identifying signal.
Figure 7:
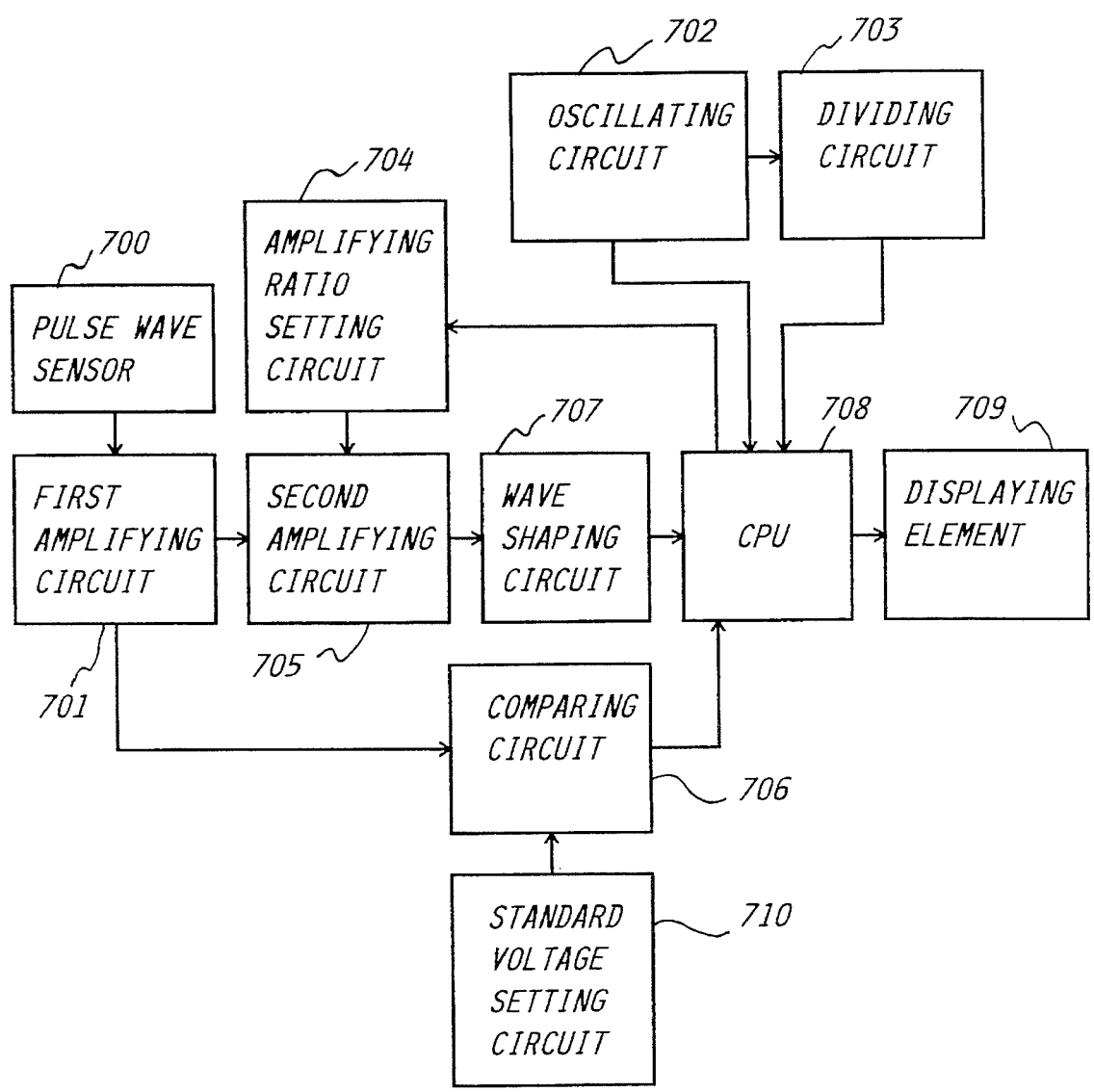
FIG. 7 is a detailed functional block diagram of the first embodiment of the present invention.

FIG. 7 shows a functional block diagram of the first practical embodiment of a pulsimeter with pedometer function according to the present invention. The pulse wave sensor 700 detects a pulse wave of a human body, and produces a corresponding pulse wave signal. The pulse wave signal is provided to the first amplifying circuit 701. The first amplifying circuit 701 amplifies the pulse wave signal and outputs the amplified pulse wave signal to the second amplifying circuit 705 and the comparing circuit 706. The comparing circuit 706 compares the amplified pulse wave signal voltage level with the standard voltage level stored in the standard voltage circuit 710, and outputs the compared result to the CPU 708 as the motion signal. The CPU 708 outputs, based on this compared result, the amplifying ratio setting signal to the amplifying ratio setting circuit 704, and outputs at the same time a signal for displaying a mode identifying mark 50 to the displaying element 709, as shown in FIG. 5. According to the mode identifying mark 50, a user can identify instantly which data is currently being measured and displayed, i.e., pulse rate data or walking pace data, by the system. The amplifying ratio setting circuit 704 sets a signal amplifying ratio for the second amplifying circuit 705, based on the amplifying ratio setting signal. The second amplifying circuit 705 improves the S/N ratio of the pulse wave signal by way of filter circuit etc., and amplifies the pulse wave signal in relation to the amplifying ratio set by the amplifying ratio setting circuit 704, then outputs the amplified pulse wave signal to the wave shaping circuit 707. The wave shaping circuit 707 transforms the pulse wave signal which is input as an analog signal into a digital signal, and outputs the digital signal to the CPU 708. The CPU 708 calculates the time interval between consecutive pulse wave signals which are transformed to digital signals by the wave shaping circuit 707, based on a timing clock signal from the dividing circuit 703, and outputs the result to the displaying element 709, such as a liquid crystal panel, or the like.

Figure 9:
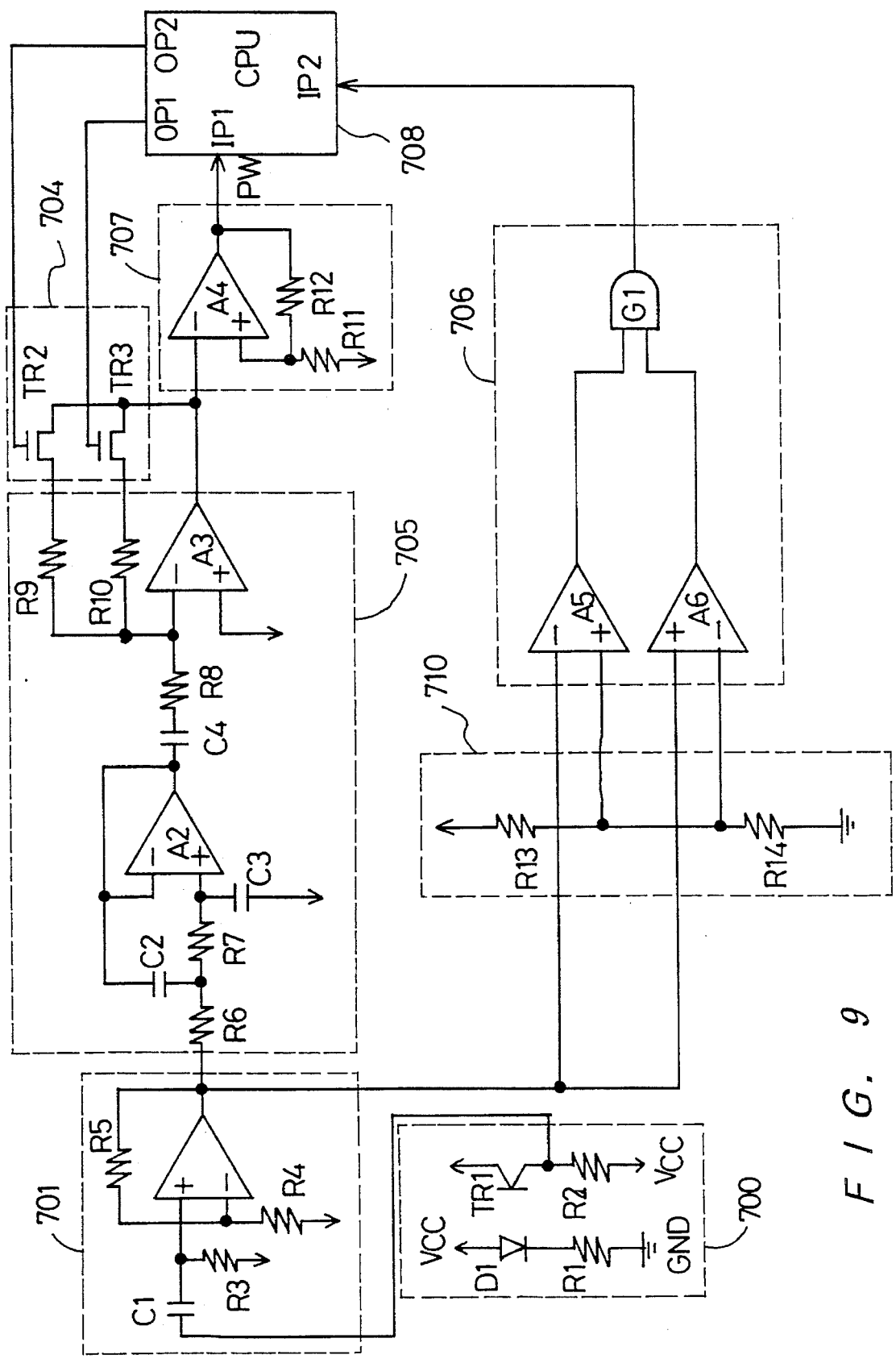
FIG. 9 is a circuit schematic diagram of am embodiment of the present invention.

FIG. 9 is a detailed circuit schematic diagram of a pulse meter with pedometer function having the functional block diagram shown in FIG. 7. The pulse wave sensor 700 detects a change in the user's blood stream using, for example, an optical device. That is, a light sensing element TR1, such as a photo-transistor or the like detects transmitted light or reflected light from a light emitting element D1 such as an LED, or the like. For example, a fingertip shaped sensor holder, which houses pulse wave sensor 700, is installed on the user' fingertip with a predetermined pressure. This pulse wave sensor 700 can detect changes in the blood stream condition in the user' fingertip.

A microphone, or the like, may also be used as the pulse wave detecting means, for detecting the cardiac sound of the user. As described above, the pulse wave sensor 700 detects a pulse wave from a human body, and outputs the detected pulse wave signal to the first amplifying circuit 701. The first amplifying circuit 701 rejects a direct current component from the pulse wave signal using a filter circuit composed of the capacitor C1 and the resistor R3, and amplifies through the non-inverting amplifier A1 comprised of an operational amplifier, then outputs the pulse wave signal to the second amplifying circuit 705 and the comparing circuit 706. The standard voltage circuit 710 sets a standard voltage using the resistors R13 and R14, and outputs the standard voltage to the comparing circuit 706.

The comparing circuit 706 comprises window-comparators A5 and A6 for the purpose of discriminating the amplitude level of the detected pulse wave signal. By comparing the pulse wave signal voltage level with the standard voltage set by the voltage dividing network of the resistors 13 and 14, the comparing circuit 706 determines whether the detected pulse wave signal reflects an at rest condition of a user or a walking condition of the user. In this case, the judgement proceeds as follows: when the output of the gate circuit G1 is at a VCC level, the user is determined to be in an at rest condition; and when the output of the gate circuit G1 is at a GND level, the user is determined to be in a walking condition. As will be understood, the amplifying ratio of the first amplifying circuit 701 and/or the voltage dividing ratio of the standard voltage setting circuit 701 may be appropriately changed such that a running condition as well as a walking condition of the user can also be determined.

Figure 10:
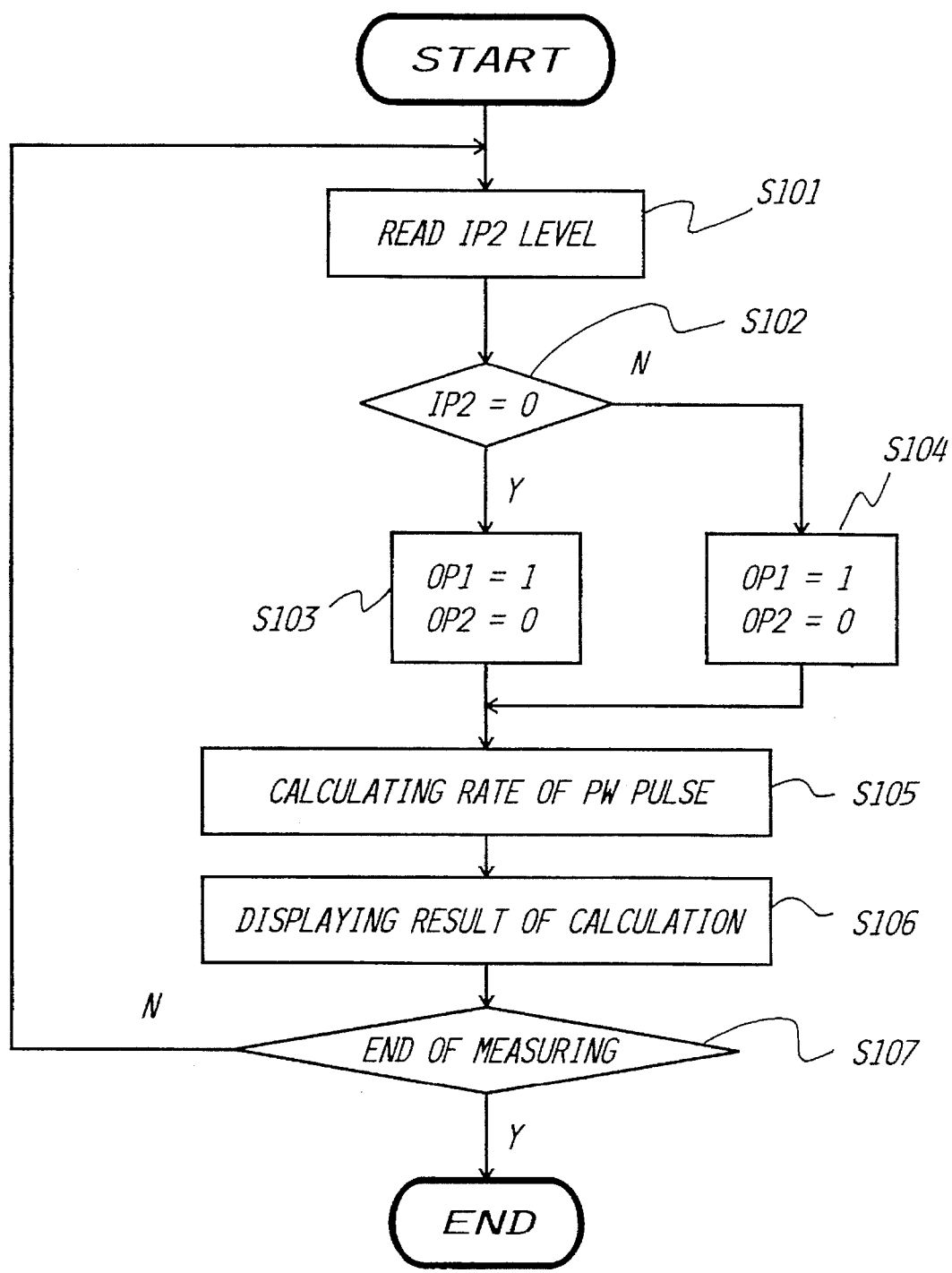
FIG. 10 is a flow chart of amplifying ratio setting procedure in the CPU of an embodiment of the present invention.

FIG. 10 is a flow chart of a procedure in which the CPU 708 controls the amplifying ratio setting circuit 704, based on the motion signal P/W which is output by the comparing circuit 706, and in which the pulse wave signal rate is output to the display element. In FIGS. 9 and 10, the CPU 708 reads the signal level at the input port IP2 and judges its level (S101, S102). When the signal is at a GND level, the resistor 10 is selected by activating the transistor TR3. When the signal is at a VCC level, the resistor R9 is selected by activating the transistor TR2 (S103, S104).

In FIG. 9, a noise component included in the pulse wave signal which is input to the second amplifying circuit 705 is rejected by the filter circuit which comprises resistors R6, and R7, capacitors C2 and C3, and an operational amplifier A2. After rejection of the noise component, the pulse wave signal is amplified by an inverting amplifier which comprises an operational amplifier A3 and resistors R8, R9 and R10. The wave shaping circuit 707 then converts the amplified pulse wave signal into a digital signal P/W, and then outputs the digital signal P/W to the input port IP1 terminal of the CPU 708. At this occasion as shown in this embodiment, it can be possible that a noise is rejected by adding hysteresis characteristics by way of positive feedback from an output of the operational amplifier through resistor R12.

In FIG. 10, the CPU 708 calculates a rate of the inputted P/W pulse based on the timing clock signal (S105). Concerning how to calculate above, a time interval between the former PW pulse and current PW pulse can simply be measured or, alternatively, time intervals between multiple numbers of PW pulses may be measured and averaged. Any result above is displayed on the displaying element 709 as a number of signals per minute (S106). After the displaying action, the measurement is continued when a continuous measuring mode is set. Alternatively, automatic stoppage of measurement after measuring for a certain period of time can also be an alternative.

(2) The second practical embodiment

Figure 8:
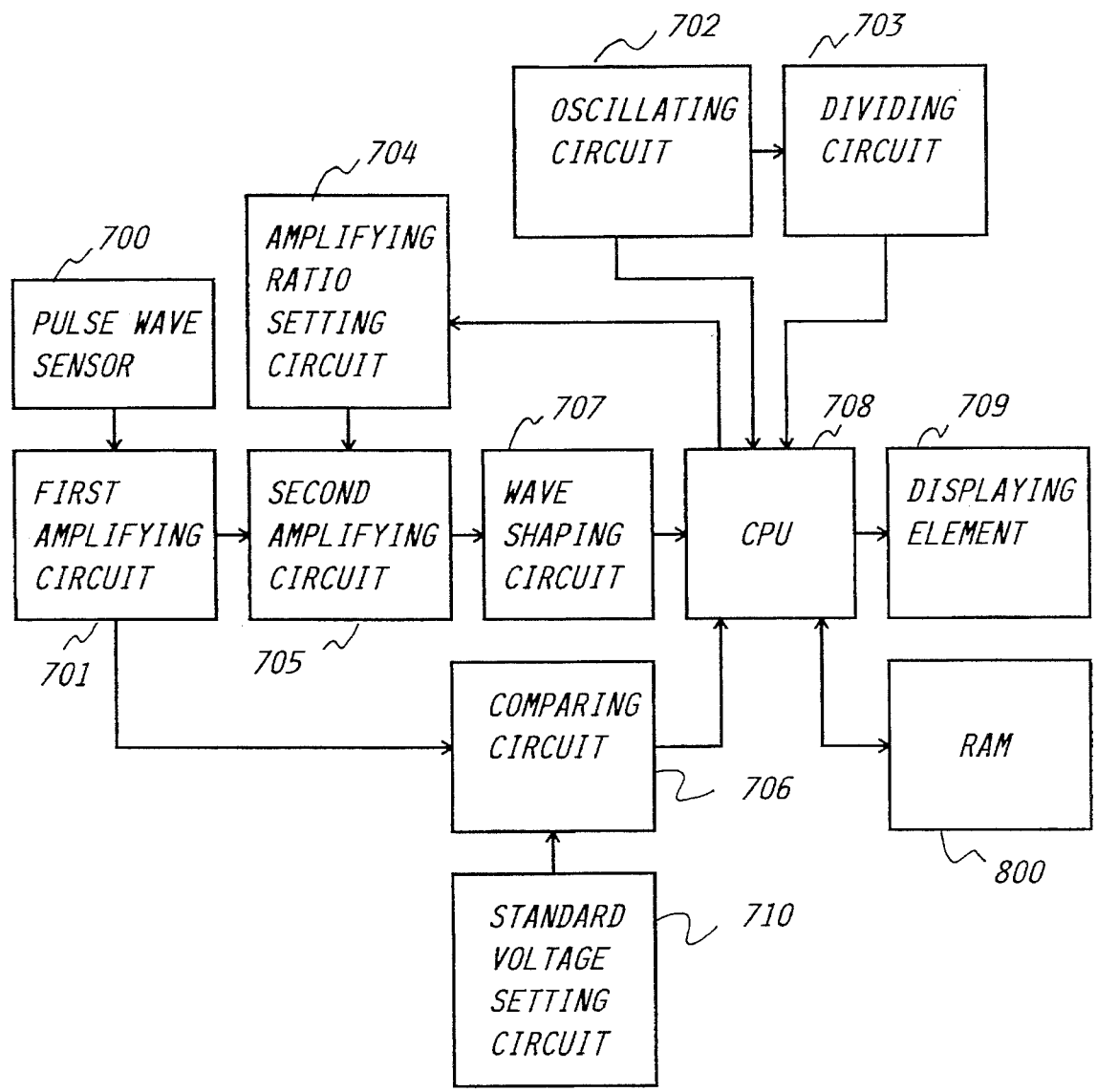
FIG. 8 is a detailed functional block diagram of a second embodiment of the present invention.

FIG. 8 is a detailed functional block diagram of the second embodiment of the pulsimeter with pedometer function of the present invention. A RAM 800 used for data memory is added to the previous embodiment shown in FIG. 7. The RAM 800 is efficiently utilized throughout its total memory area by dividing its use as, for example, a PW pulse memory area, a rate calculating area, a graphic data memory area, a step length memory area, and a distance calculating area.

Figure 11:
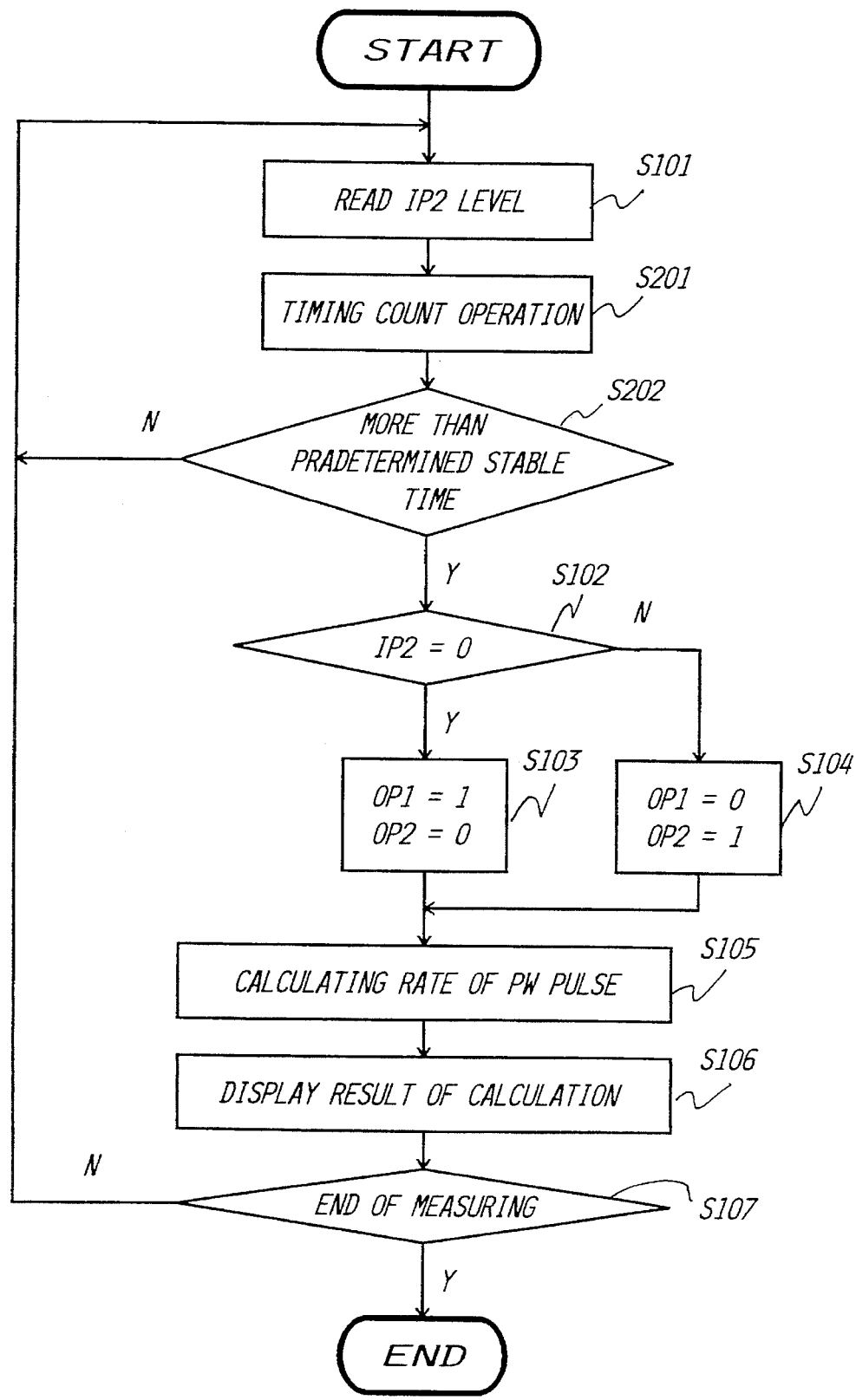
FIG. 11 is a flow chart of the motion detecting procedure in the CPU of an embodiment of the present invention.

FIG. 11 shows a flow chart of a procedure in which a stable time duration of the motion signal P/W detected by the comparing circuit 706 is measured and in which the amplifying ratio setting circuit 704 is controlled by the CPU 708. The motion signal P/W is read from input port IP2, and when its level is at the same level as that of the former one, a time counting operation is executed. The time counting is executed in the time counting area which is previously allocated in the RAM 800. On the other hand, when the input level is different from that of the former pulse, the counted time content is reset and time duration is counted again from the start (S201). When the counted time duration exceeds a predetermined time, the calculating and displaying procedure is followed as shown in FIG. 10 (S202). Due to the above procedure, the displayed content is not instantly altered by a momentary change in the motion signal, and the user can be confident in the displayed value.

Figure 6:
FIG. 6 is an example of a graphical display.
Figure 12:
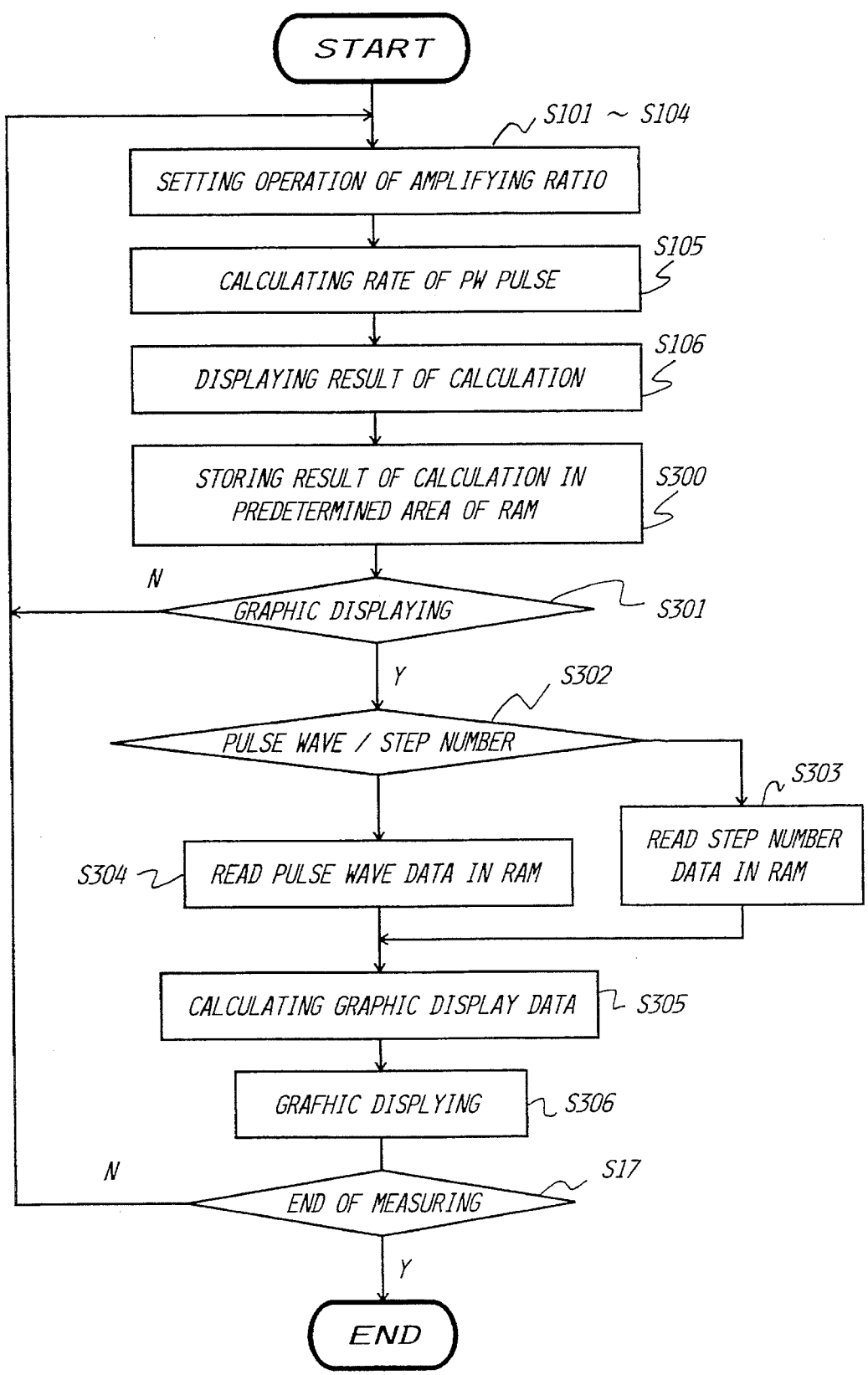
FIG. 12 is a flow chart of the graphical display procedure in the CPU of an embodiment of the present invention.

FIG. 12 is a flow chart of a graphical display, e.g., a time series display procedure of a rate calculation result of the detected pulse wave signal. After the rate calculation and displaying procedure shown in FIG. 10 is performed, the result is stored in the previously allocated PW pulse memory area in the RAM 800 (S300). After this procedure, a judgment is made whether a graphical display mode is selected or not (S301). When a graphical display mode is selected, another judgment is made as to what kind of data should be displayed (S304), then stored data in the RAM 800 is converted to displayable graphic data (S305). And then, for example, as shown in FIG. 6, a time series graph is displayed (S306). By way of change in calculation procedure, a flicker display of the smallest or the largest value may be performed or a display with a sweeping function may also be performed in the case when the display is not completed at once.

Figure 13:
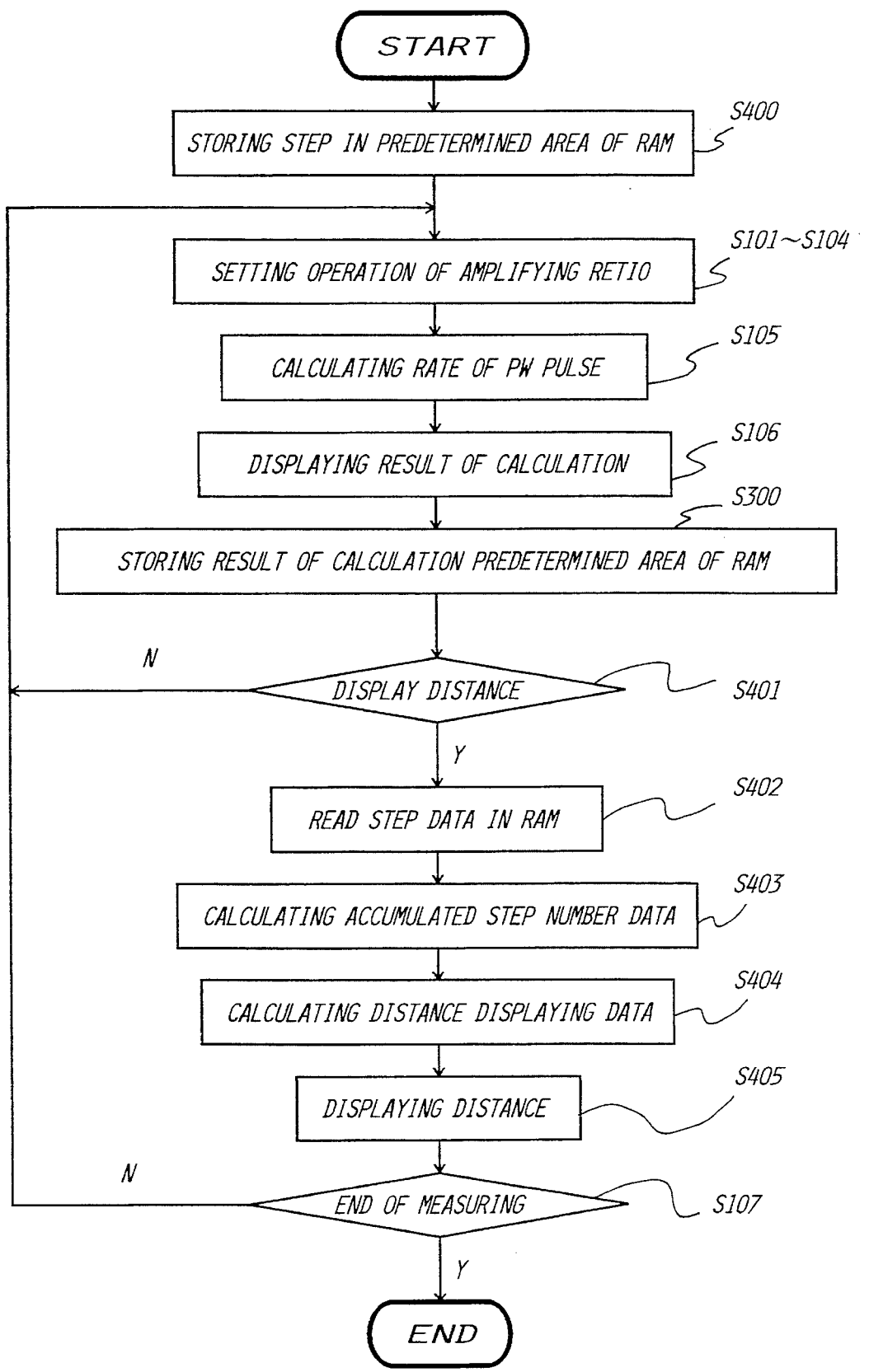
FIG. 13 is a flow chart of the distance calculating and displaying procedure in the CPU of an embodiment of the present invention.

FIG. 13 is a flow chart of a display procedure in the display element 709 by way of distance calculation utilizing step length data and cumulative step number data stored in RAM 800. At first, the step length is preset in the step length data memory allocation area in the RAM 800 (S400). Next, after the rate calculation and its display procedure shown in FIG. 10, the result of calculation is stored in the PW pulse memory allocation area in the RAM 800 (S300). After a judgment is made as to whether a distance display mode is selected or not (S401), reading of the step length data stored in the RAM 800 (S402) and distance calculation by cumulative step number data stored in the other area in the RAM 800 are carried out (S404). The result is then displayed on the display element 709 (S405). Moreover, not only the distance but also time series shift type display of the cumulative distance can be displayed graphically by way of graphical display procedure shown in FIG. 12.

As explained above, a single pulse wave sensor can be used for pace measurement as well as pulse rate calculation in the pulsimeter with pedometer function of the present invention. This structure leads to realization of smaller sizing, and by changing the standard voltage for discriminating the signal level detected, not only walking but also running can be measured (a product in the latter style usage is called a "pitchmeter"). Therefore, various kinds of multipurpose devices in addition to those shown above can be produced according to the present invention.

What is claimed is:

1. An electronic combined pulse meter and pedometer comprising:

pulse wave detecting means for detecting an input heartbeat pulse wave and providing a corresponding detected pulse wave output signal;

clock signal generating means for generating a clock signal;

calculating means receptive of the detected pulse wave output signal and the clock signal for calculating the time interval between a predetermined number of pulses of the detected pulse wave output signal in accordance with the flock signal;

pulse wave level storing means for storing a predetermined pulse wave level for use as a reference level for discriminating whether the detected pulse wave output signal is indicative of an at rest state or a walking state of a user;

walking state detecting means for detecting whether the user is at rest or walking by comparing the detected pulse wave output signal from the pulse wave detecting means with the predetermined pulse wave level stored in the pulse wave level storing means and for providing a walking state signal when the level of the detected pulse wave output signal exceeds the predetermined pulse wave level;

constant value storing means for storing a plurality of pre-set pulse rates and walking pace values;

calculation control means for controlling the calculating means in accordance with the walking state signal, and for selecting pre-set pulse rate and walking pace values from the constant value storing means based on the calculated time interval between a predetermined number of pulses of the detected pulse wave output signal and the walking state signal; and display means receptive of the calculated time interval between a predetermined number of pulses of the pulse wave output signal and the selected pulse rate and walking pace values for selectively displaying the user' pulse rate or walking pace in accordance with the walking state signal.

2. An electronic combined pulse meter and pedometer comprising:

pulse wave detecting means for detecting an input heartbeat pulse wave and providing a corresponding detected pulse wave output signal;

clock signal generating means for generating a clock signal;

calculating means receptive of the detected pulse wave output signal and the clock signal for calculating the time interval between a predetermined number of pulses of the detected pulse wave output signal in accordance with the clock signal;

pulse wave level storing means for storing a predetermined pulse wave level for use as a reference level for discriminating whether the detected pulse wave output signal is indicative of an at rest state or a walking state of a user;

walking state detecting means for detecting whether the user is in at rest or is walking by comparing the detected pulse wave output signal from the pulse wave detecting means with the predetermined pulse wave level stored in the pulse wave level storing means and producing a walking state output signal when the level of the detected pulse wave output signal exceeds the predetermined pulse wave level;

constant value storing means for storing a plurality of pre-set pulse rate and walking pace values;

walking state counting means receptive of the walking state output signal for measuring the duration of the walking state output signal;

calculation control means for controlling the calculating means in accordance with the walking state output signal, and for selecting pre-set pulse rate and walking pace values from the constant value storing means based on the calculated time interval between a predetermined number of pulses of the detected pulse wave output signal and an output of the walking state counting means; and display means receptive of the calculated value and the selected pulse rate and walking pace values for selectively displaying the users' pulse or walking pace.

3. An electronic combined pulse meter and pedometer according to claim 1; wherein the display means further comprises means for displaying an identifying marker indicating whether the user is in an at rest state or is walking.

4. An electronic combined pulse meter and pedometer according to claim 1; further comprising calculated value storing means for storing a predetermined number of calculated values of the calculating means; and wherein the display means comprises graph calculating means for calculating data for display in a time-series graph on the display means.

5. An electronic combined pulse meter and pedometer according to claim 1; further comprising calculated value storing means for storing a predetermined number of calculated values of the calculating means; step data storing means for storing the step span of the user and successively calculated walking pace data; distance calculating means for calculating a distance which the user has walked in accordance with the stored step span data and the stored walking pace data; and wherein the display means includes means for displaying the distance which the user has walked.

6. An electronic combined pulse meter and pedometer according to claim 1; wherein the pulse wave detecting means comprises a heartbeat sensor for detecting the heartbeat of a user.

7. An electronic combined pulse meter and pedometer according to claim 6; wherein the heartbeat sensor comprises an optical sensor for detecting the heartbeat of the user by detecting changes in the blood flow of the user.

8. An electronic combined pulse meter and pedometer according to claim 6; wherein the heartbeat sensor comprises a microphone for detecting the heartbeat of the user by detecting and amplifying the cardiac sound of the user.

9. A combined electronic pulse meter and pedometer comprising: means for detecting the heartbeat of a user; means for calculating the time interval between a predetermined number of pulses of the users' heartbeat and for selectively determining pulse rate or walking pace data in accordance with the calculated time interval; means for producing a walking state signal when the detected heartbeat is above a predetermined level; control means for controlling the calculating means to determine pulse rate data when the level of the detected heartbeat is not above the predetermined level and for determining a walking pace when the level of the detected heartbeat is above the predetermined level; and display means for selectively displaying pulse rate data and walking pace data in accordance with the calculated time interval and the walking state output signal.

10. A combined electronic pulse meter and pedometer according to claim 9; further comprising storing means for storing pulse rate data and walking pace data corresponding to respective calculated time intervals; and wherein the calculation control means controls the calculating means to select pulse rate data corresponding to the calculated time interval when the level of a predetermined number of pulses of the detected heartbeat are not greater than the predetermined level and for selecting walking pace data when the level of a predetermined number of pulses of the detected heartbeat are greater than the predetermined level.

11. A combined electronic pulse meter and pedometer according to claim 9; further comprising counting means for producing a count output signal when the detected heartbeat maintains a predetermined level for at least a predetermined time and wherein the displaying means includes means for displaying the stored data only when a count output signal is produced.

12. A combined electronic pulse meter and pedometer according to claim 9; further comprising calculated data storing means for storing calculated pulse rate and walking pace data; and wherein the display means includes means for providing a time-series display of the users' pulse rate and walking pace.

13. A combined electronic pulse meter and pedometer according to claim 9; wherein the means for detecting the heartbeat of the user comprises a heartbeat sensor for measuring the users' heartbeat and producing a corresponding pulse output signal and wherein the means for calculating the time interval between a predetermined number of pulses of the users' heartbeat comprises clock signal generating means for generating a clock signal and calculating means for calculating the time period in accordance with the pulse output signal and the clock signal.

14. A combined electronic pulse meter and pedometer according to claim 9; wherein the means for detecting the heartbeat of the user comprises an optical device for detecting changes in the users' blood flow and producing a corresponding pulse output signal in accordance therewith.

15. A combined electronic pulse meter and pedometer according to claim 9; wherein the means for detecting the heartbeat of the user comprises a microphone for detecting the cardiac sound of the user and producing a corresponding pulse output signal.

16. A combined electronic pulse meter and pedometer according to claim 9; wherein the display means includes means for displaying a mode indicator for indicating whether the displayed data is the users' pulse rate or walking pace.

17. A combined electronic pulse meter and pedometer according to claim 9; further comprising calculated value storing means for storing calculated values of the calculating means; walking span data storing means for storing walking span data used for calculating a walking distance of the user.

18. A combined electronic pulse meter and pedometer according to claim 9; wherein the means for determining whether the level of the detected heartbeat is above a predetermined level comprises comparator means for comparing the detected heartbeat with a reference signal having the predetermined level.

19. A combined electronic pulse meter and pedometer according to claim 9; wherein the means for detecting the user' heartbeat includes sensing means for sensing a pulse wave signal representing the users' heartbeat and producing a corresponding pulse wave output signal; and the calculating means comprises a microprocessor receptive of the pulse wave output signal and the clock signal.

* * * * *